United States Patent [19]

Rowlette

[11] Patent Number: 5,040,417
[45] Date of Patent: Aug. 20, 1991

[54] ELECTRONIC RELATIVE HUMIDITY/TEMPERATURE MEASURING SYSTEM

[76] Inventor: Mitchell R. Rowlette, 152 Ridge Ave., Berea, Ky. 40403

[21] Appl. No.: 434,288

[22] Filed: Nov. 13, 1989

[51] Int. Cl.$^5$ .............................................. G01N 25/56
[52] U.S. Cl. .................................. 73/336.5; 324/694; 338/35
[58] Field of Search ........................... 73/336.5, 29.02; 324/694; 338/35

[56] References Cited

U.S. PATENT DOCUMENTS

| | | | |
|---|---|---|---|
| 3,196,682 | 7/1965 | Johnson, Jr. ........................ | 73/336.5 |
| 3,797,312 | 3/1974 | Campbell ............................ | 73/336.5 |
| 4,379,406 | 4/1983 | Bennewitz et al. ................. | 73/336.5 |
| 4,816,748 | 3/1989 | Tazawa et al. ..................... | 73/336.5 X |

FOREIGN PATENT DOCUMENTS

| | | | |
|---|---|---|---|
| 104749 | 8/1980 | Japan .................................. | 73/336.5 |
| 80847 | 3/1989 | Japan .................................. | 73/336.5 |

Primary Examiner—Hezron E. Williams
Assistant Examiner—Joseph W. Roskos

[57] ABSTRACT

The disclosure relates to a system for measuring relative humidity and temperature wherein there are provided three controlled switching matrices, a first of the matrices determining whether a current for determining temperature or relative humidity is to be fed via a diode to a system voltage output from when the voltage output will be converted to an appropriate temperature or relative humidity reading. The remaining two matrices are each controlled by an oscillating voltage which alternates the output or input terminal thereof depending upon whether the oscillating voltage is positive or negative. This causes current to be passed through a humidity responsive resistor in opposite directions during each half cycle of the oscillating voltage. In the case of humidity sensing, the diode used for measuring temperature also acts as a temperature compensating device for the humidity sensor, thereby having a dual function in the system.

15 Claims, 2 Drawing Sheets

ELECTRONIC RELATIVE HUMIDITY/TEMPERATURE MEASURING SYSTEM

BACKGROUND OF THE INVENTION

1. Field of the Invention

This invention relates to a system for measuring temperature and relative humidity and, more specifically, to an electronic, low cost relative humidity temperature measurement system.

2. Brief Description of the Prior Art

Some of the most reliable, cost effective and miniature relative humidity sensors available are based upon water absorptive polymers. The major drawbacks to these sensors include temperature sensitivity, the need for low cost AC stimulation and non-linear response to relative humidity. These problems dictate that electronics must be employed to condition the sensor's response. To compensate for temperature sensitivity, these electronics must employ some form of temperature measuring device, such as a thermistor. The use of AC stimulation to the relative humidity sensor brings present two distinct problems. First, almost all highly integrated electronics are powered by DC voltages. This implies that the DC power must be converted to AC power for the sensor. The amplitude of the AC power is also temperature sensitive unless some form of amplitude feedback control is used, the latter generally being expensive. Second, stimulation of a relative humidity sensor with AC power requires that the AC signal from the sensor be converted back to DC. This requires filtering and, usually, rectification. The non-linear response of the the relative humidity sensor requires signal linearization and calibration. Correction of these problems is generally, quite expensive.

For HVAC application or any "comfort control", it is always desirable to measure temperature in addition to relative humidity. In general, this requires an additional temperature sensor and output circuitry.

SUMMARY OF THE INVENTION

In accordance with the present invention, the above noted problems of the prior art are minimized.

Briefly, in accordance with the present invention, there are provided three controlled switching matrices, a first of the matrices determining whether a current for determining temperature or relative humidity is to be fed via a diode to a system voltage output from whence the voltage output will be converted to an appropriate temperature or relative humidity reading. The remaining two matrices are each controlled by a oscillating voltage which alternates the output or input terminal thereof depending upon whether the oscillating voltage is positive or negative. This causes current to be passed through a humidity responsive resistor in opposite directions during each half cycle of the oscillating voltage. In the case of humidity sensing, the diode used for measuring temperature also acts as a temperature compensating device for the humidity sensor and linearizes the humidity sensor response, thereby having a dual function in the system.

DESCRIPTION OF THE PREFERRED EMBODIMENT

Figure 1:
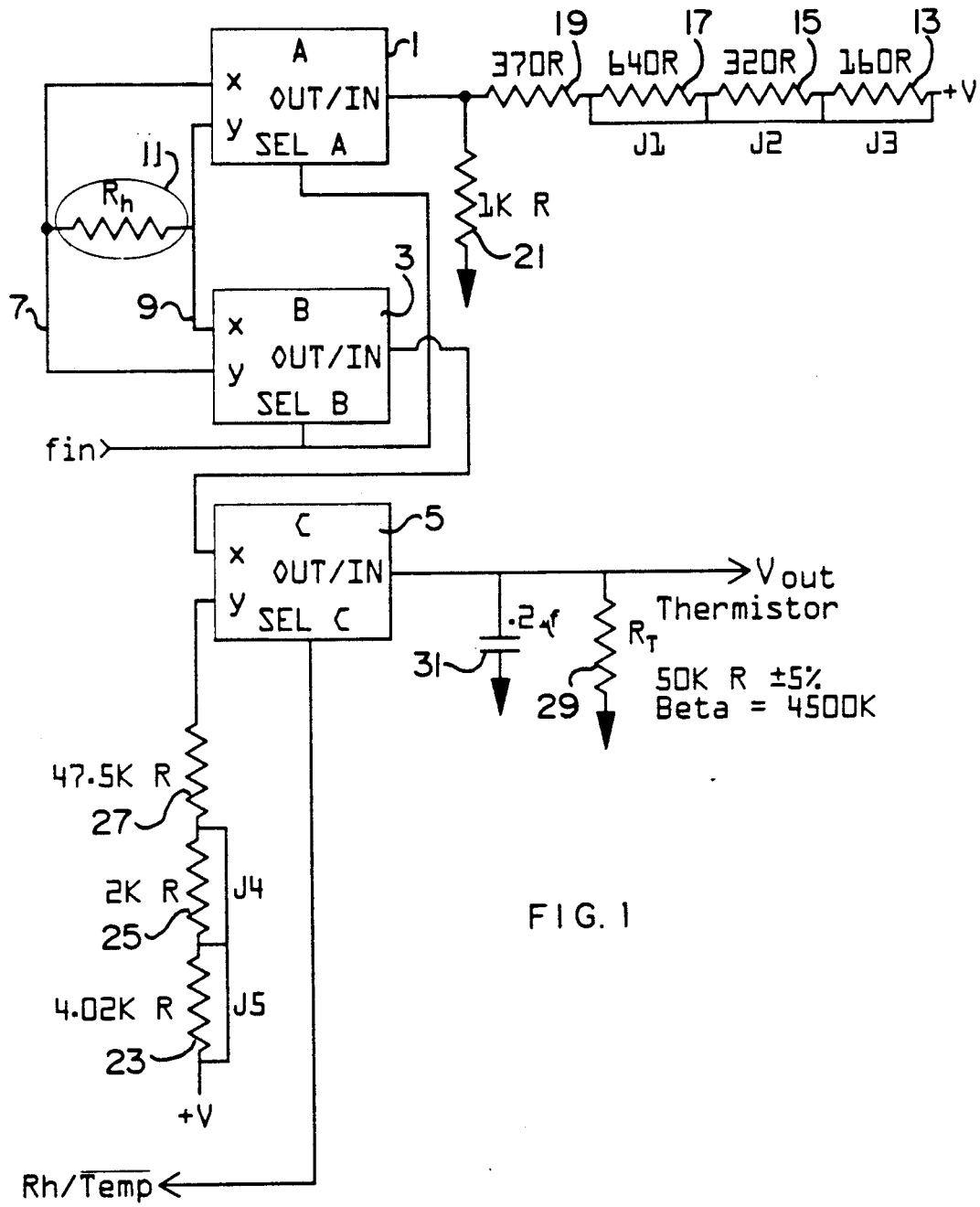
FIG. 1 is a circuit diagram of a relative humidity/temperature measuring system in accordance with the present invention.

Referring to FIG. 1, there is shown a circuit diagram of a relative humidity/temperature measuring system in accordance with the present invention.

The system includes three identical switch matrices 1, 3 and 5, each matrix being one third of a CD4053 semiconductor chip. Each switch matrix includes an input/output terminal, x and y terminals which can be used for input or output and a select terminal which opens one of the x and y terminals and closes the other of the x and y terminals. The x terminal of matrix 1 is coupled to the y terminal of matrix 3 via a conductor 7 and the x terminal of matrix 3 is coupled to the y terminal of matrix 1 via a conductor 9. The conductors 7 and 9 are coupled by a relative humidity sensor 11 which is preferably a resistor, the resistance of which changes with change in relative humidity according to a known an repeatable function. A voltage source V+ provides an input to the matrix 1 at the output/input terminal thereof via a voltage divider composed of a plurality of serially connected jumpered resistors 13, 15 and 17, and resistor 19 and a further resistor 21. One or more of the jumpers across resistors 13, 15 and/or 17 can be removed to alter the resistance from the voltage source V+ to the output/input terminal and thereby change the voltage at the output/input terminal to match the particular humidity sensor 11. The select terminals of the matrices 1 and 3 are controlled by a preferably oscillating voltage Fin which is preferably a 1 kHz. square wave. When this voltage is low, the x terminals of matrices 1 and 3 are closed and the y terminals of these matrices are open. Conversely, then this voltage is high, the x terminals of the matrices 1 and 3 are open and the y terminals of these matrices are closed.

The third matrix 5 also has an output/input terminal coupled to the system output Vout, an x terminal coupled to the input/output terminal of matrix 3, a y terminal coupled to a voltage supply V+ via a series of jumpered resistors 23 and 25 and a further resistor 27. As discussed above, the voltage applied to the y terminal of matrix 5 is determined by the number of jumpers which are removed. This voltage is selected in accordance with the diode 29 selected. The selection terminal is operated by a HUMIDITY/TEMPERATURE input wherein a high voltage causes a relative humidity measurement to be taken and a low voltage causes a temperature measurement to be taken. This is because the high voltage thereon will open the x terminal and close the y terminal whereas a low voltage thereon will close the x terminal and open the y terminal. The diode 29 is coupled between the output/input terminal of matrix 5 and reference voltage. Capacitor 31 acts as a filter.

To measure temperature, the voltage applied to the selection terminal of matrix 5 is high, thereby opening the x terminal thereof and closing the y terminal thereof. Accordingly, current will flow from the voltage source V+ through the resistor 27 and none, one or both of resistors 23 and 25, through the matrix 5 to the output Vout. The output voltage is determined by the voltage across the diode 29, this voltage varying due to the change of conductivity of the diode due to temperature. This voltage is converted to a temperature reading by circuitry (not shown) of well known type.

To measure relative humidity, the voltage applied to the selection terminal of matrix 5 is low, thereby closing the x terminal thereof and opening the y terminal thereof. Therefore, when the voltage at Fin is low, the x terminals in the matrices 1 and 3 will close and the y terminals of these matrices will open. This permits current from the voltage source V+ to travel through resistors 19 and 21 and none, one, two or all three of resistors 13, 15 and 17 and provide a voltage at the output/input terminal of matrix 1 in accordance therewith. This current will pass to the x terminal of matrix 1, through the relative humidity sensor 11 to the x terminal of matrix 3, through the output/input terminal of matrix 3 to the x terminal of matrix 5 and then to the Vout output of the system via the output/input terminal of matrix 5. The amount of current flow at the output/input terminal of matrix 5 is determined by the resistance of the relative humidity sensor 7. The diode 29 provides compensation for the temperature dependence of the relative humidity sensor 11 as well as providing a load for the current at the output/input terminal of matrix 5. The voltage across the diode 29 is applied to the system output terminal Vout, this voltage being converted to a relative humidity reading by circuitry (not shown) of well known type.

When the voltage at Fin is high during the second portion of the square wave, the x terminals in the matrices 1 and 3 will open and the y terminals of these matrices will close. This permits current from the voltage source V+ to travel through resistors 19 and 21 and none, one, two or all three of resistors 13, 15 and 17 and provide a voltage at the output/input terminal of matrix 1 in accordance therewith. This current will pass to the y terminal of matrix 1, through the relative humidity sensor 11 to the x terminal of matrix 3, through the output/input terminal of matrix 3 to the x terminal of matrix 5 and then to the Vout output of the system via the output/input terminal of matrix 5. This causes a true alternating current to pass through the humidity sensor 11 while maintaining a constant DC voltage at the system output Vout.

Figure 2:
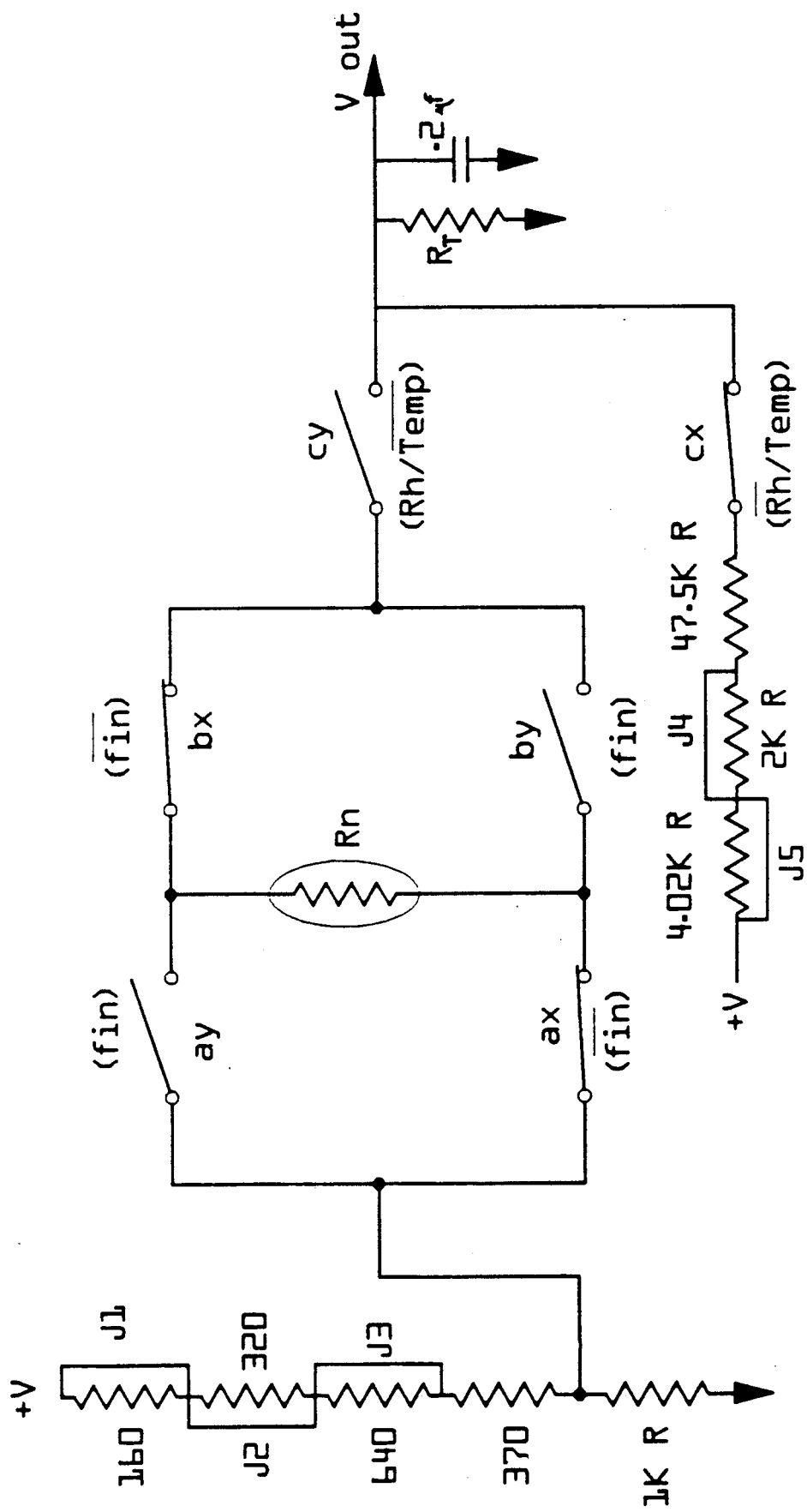
FIG. 2 is a simplified diagram of the operation of the circuit of FIG. 1.

Referring to FIG. 2, there is shown is simplified circuit diagram of the operation of the circuit of FIG. 1. In this figure, ax and ay indicate the state (open or closed) of the terminals x and y of matrix 1, bx and by indicate the state of the terminals x and y of matrix 3 and cx and cy indicate the state of the selection terminal of the matrix 7.

Though the invention has been described with respect to a specific preferred embodiment thereof, many variation and modifications will immediately become apparent to those skilled in the art. It is therefore the intention that the appended claims be interpreted as broadly as possible in view of the prior art to include all such variations and modifications.

I claim:

1. A parameter measuring system comprising:
   (a) a first switch having first and second input terminals, an output terminal and an input selecting terminal responsive to a predetermined signal applied thereto to open one of said first and second input terminals and close the other of said first and second input terminals;
   (b) a diode coupled to said output terminal; and
   (c) a humidity responsive circuit coupled to said first input terminal.

2. The system of claim 1 further including a source of voltage for applying a voltage to said second input terminal.

3. The system of claim 2 wherein said voltage is variable.

4. The system of claim 3 wherein said humidity responsive circuit includes a humidity controlled electrical resistive element and switch means to cause current to pass through said resistive element in opposite directions as a function of time.

5. The system of claim 4 wherein the switch means of said humidity responsive circuit includes second and third switches responsive to a predetermined signal thereto and coupled to said resistive element to cause said current to pass through said resistive element in opposite directions as a function of time.

6. The system of claim 5 wherein said second switch includes a voltage input terminal, first and second output terminals and an output selecting terminal responsive to a predetermined signal applied thereto to open one of said first and second output terminals and close the other of said first and second output terminals and said third switch includes first and second input terminals, and output terminal and an input selecting terminal responsive to said predetermined signal applied thereto to open one of said first and second input terminals.

7. The system of claim 6, further including first connecting means coupling one of said output terminals of said second switch to one of said input terminals of said third switch and second connecting means coupling the other of said output terminals of said second switch to the other of said input terminals of said third switch, said humidity controlled electrical resistive element being coupled between said first and second connecting means.

8. The system of claim 2 wherein said humidity responsive circuit includes a humidity controlled electrical resistive element and switch means to cause current to pass through said resistive element in opposite directions as a function of time.

9. The system of claim 8 wherein the switch means of said humidity responsive circuit includes second and third switches responsive to a predetermined signal thereto and coupled to said resistive element to cause said current to pass through said resistive element in opposite directions as a function of time.

10. The system of claim 9 wherein said second switch includes a voltage input terminal, first and second output terminals and an output selecting terminal responsive to a predetermined signal applied thereto to open one of said first and second output terminals and close the other of said first and second output terminals and said third switch includes first and second input terminals, and output terminal and an input selecting terminal responsive to said predetermined signal applied thereto to open one of said first and second input terminals.

11. The system of claim 10, further including first connecting means coupled to one of said output terminals of said second switch to one of said input terminals of said third switch and second connecting means coupling the other of said output terminals of said second switch to the other of said input terminals of said third switch, said humidity controlled electrical resistive element being coupled between said first and second connecting means.

12. The system of claim 1 wherein said humidity responsive circuit includes a humidity controlled electrical resistive element and switch means to cause current to pass through said resistive element in opposite directions as a function of time.

13. The system of claim 12 wherein the switch means of said humidity responsive circuit includes second and third switches responsive to a predetermined signal thereto and coupled to said resistive element to cause said current to pass through said resistive element in opposite directions as a function of time.

14. The system of claim 13 wherein said second switch includes a voltage input terminal, first and second output terminals and an output selecting terminal responsive to a predetermined signal applied thereto to open one of said first and second output terminals and close the other of said first and second output terminals and said third switch includes first and second input terminals, and output terminal and an input selecting terminal responsive to said predetermined signal applied thereto to open one of said first and second input terminals.

15. The system of claim 14, further including first connecting means coupling one of said output terminals of said second switch to one of said input terminals of said third switch and second connecting means coupling the other of said output terminals of said second switch to the other of said input terminals of said third switch, said humidity controlled electrical resistive element being coupled between said first and second connecting means.

* * * * *